United States Patent
Abrahams et al.

(10) Patent No.: US 8,636,774 B2
(45) Date of Patent: Jan. 28, 2014

(54) SPINAL IMPLANT APPARATUSES AND METHODS OF IMPLANTING AND USING SAME

(75) Inventors: John M. Abrahams, Scarsdale, NY (US); Peter J. Amarosa, Dover, NH (US); Michael Leatherman, Dover, NH (US)

(73) Assignee: Spinal USA, Inc., Parsippany, NJ (US)

( * ) Notice: Subject to any disclaimer, the term of this patent is extended or adjusted under 35 U.S.C. 154(b) by 289 days.

(21) Appl. No.: 12/971,620

(22) Filed: Dec. 17, 2010

(65) Prior Publication Data
US 2012/0158060 A1    Jun. 21, 2012

(51) Int. Cl.
*A61B 17/70* (2006.01)

(52) U.S. Cl.
USPC ............................. 606/250; 606/249

(58) Field of Classification Search
USPC ......................... 606/246, 248–253
See application file for complete search history.

(56) References Cited

U.S. PATENT DOCUMENTS

| | | | |
|---|---|---|---|
| 5,709,684 A | 1/1998 | Errico et al. | |
| 6,217,578 B1 * | 4/2001 | Crozet et al. | 606/252 |
| 6,238,396 B1 | 5/2001 | Lombardo | |
| 6,419,703 B1 | 7/2002 | Fallin et al. | |
| 6,524,310 B1 | 2/2003 | Lombardo et al. | |
| 6,902,580 B2 | 6/2005 | Fallin et al. | |
| 7,566,345 B1 | 7/2009 | Fallin et al. | |
| 8,066,741 B2 * | 11/2011 | Fallin et al. | 606/248 |
| 2001/0047171 A1 | 11/2001 | Troxell et al. | |
| 2002/0007183 A1 * | 1/2002 | Lee et al. | 606/61 |
| 2003/0018334 A1 | 1/2003 | Richelsoph et al. | |
| 2004/0116928 A1 | 6/2004 | Young et al. | |
| 2005/0010291 A1 | 1/2005 | Stinson et al. | |
| 2005/0033434 A1 | 2/2005 | Berry | |
| 2005/0228377 A1 | 10/2005 | Chao et al. | |
| 2005/0228382 A1 * | 10/2005 | Richelsoph et al. | 606/61 |
| 2006/0015181 A1 * | 1/2006 | Elberg | 623/16.11 |
| 2006/0206114 A1 * | 9/2006 | Ensign et al. | 606/61 |
| 2008/0281360 A1 * | 11/2008 | Vittur et al. | 606/248 |
| 2008/0281361 A1 * | 11/2008 | Vittur et al. | 606/249 |
| 2009/0138047 A1 * | 5/2009 | McBride et al. | 606/251 |
| 2010/0069960 A1 * | 3/2010 | Chaput | 606/249 |
| 2010/0174315 A1 * | 7/2010 | Scodary et al. | 606/248 |
| 2010/0249842 A1 * | 9/2010 | Mir | 606/250 |
| 2011/0307012 A1 * | 12/2011 | Mir et al. | 606/251 |

FOREIGN PATENT DOCUMENTS

| | | |
|---|---|---|
| EP | 1093761 | 4/2001 |
| WO | WO 99/23962 | 5/1999 |
| WO | WO 02-30307 | 4/2002 |

OTHER PUBLICATIONS

International Search Report and Written Opinion for PCT/US2011/065694, mailed Aug. 22, 2012, 12 pages.

* cited by examiner

*Primary Examiner* — Ellen C Hammond
(74) *Attorney, Agent, or Firm* — Knobbe, Martens, Olson & Bear LLP

(57) ABSTRACT

An adjustable spinal implant device, comprising: a sliding portion provided with a tongue; and, a non-sliding portion provided with a slot adapted for receipt of the tongue; wherein the tongue is slidably and rotatably positioned within the slot.

39 Claims, 9 Drawing Sheets

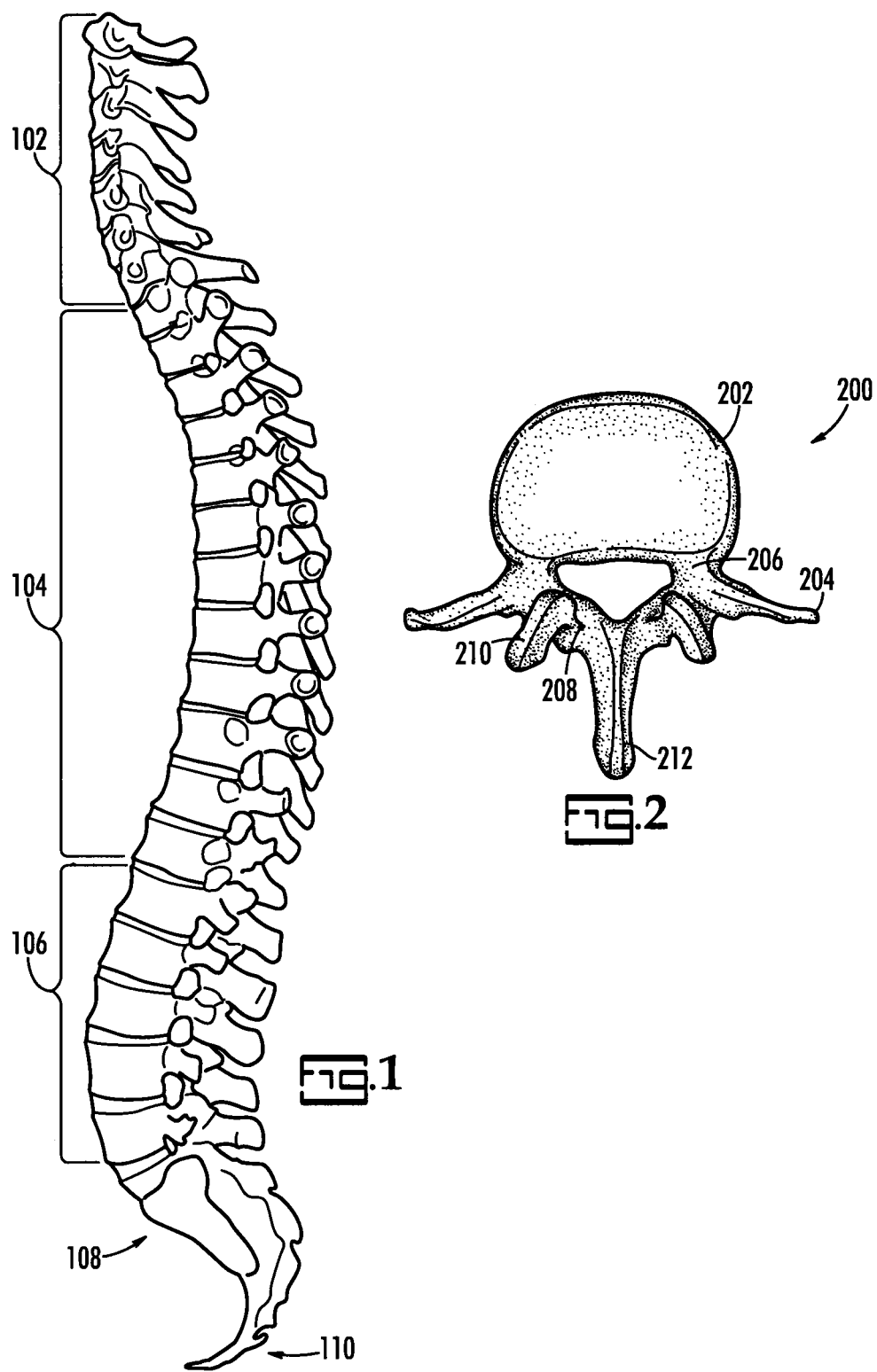

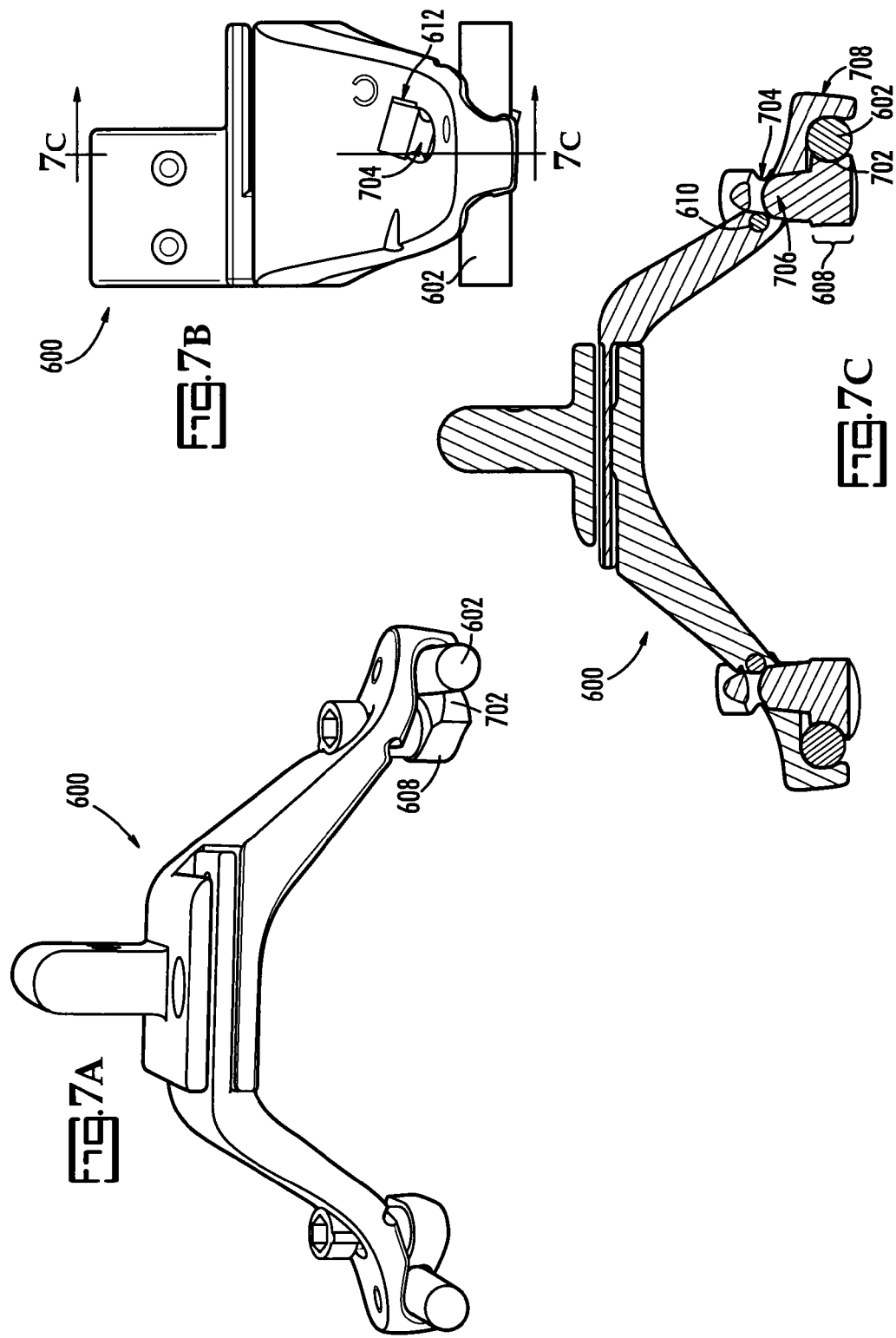

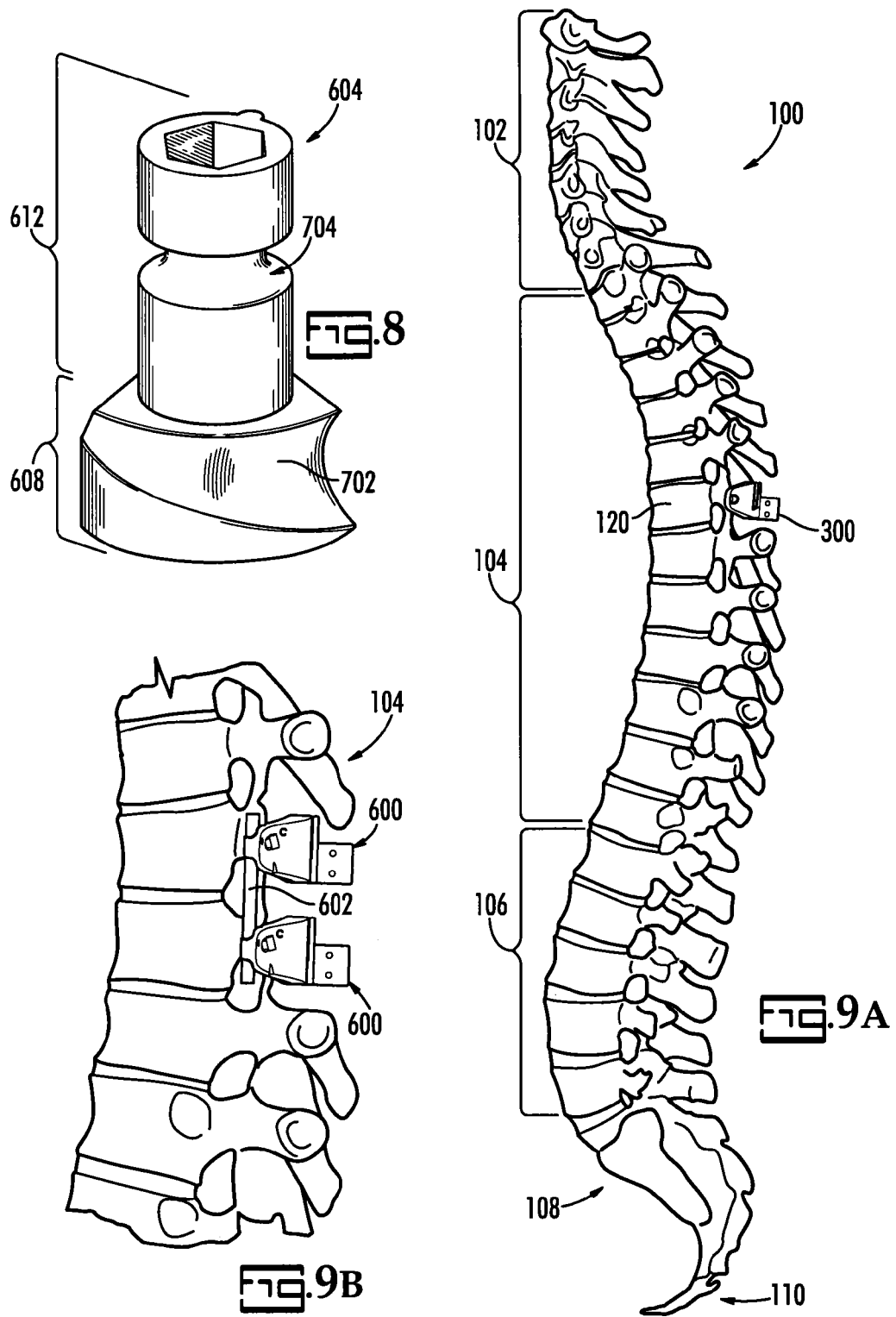

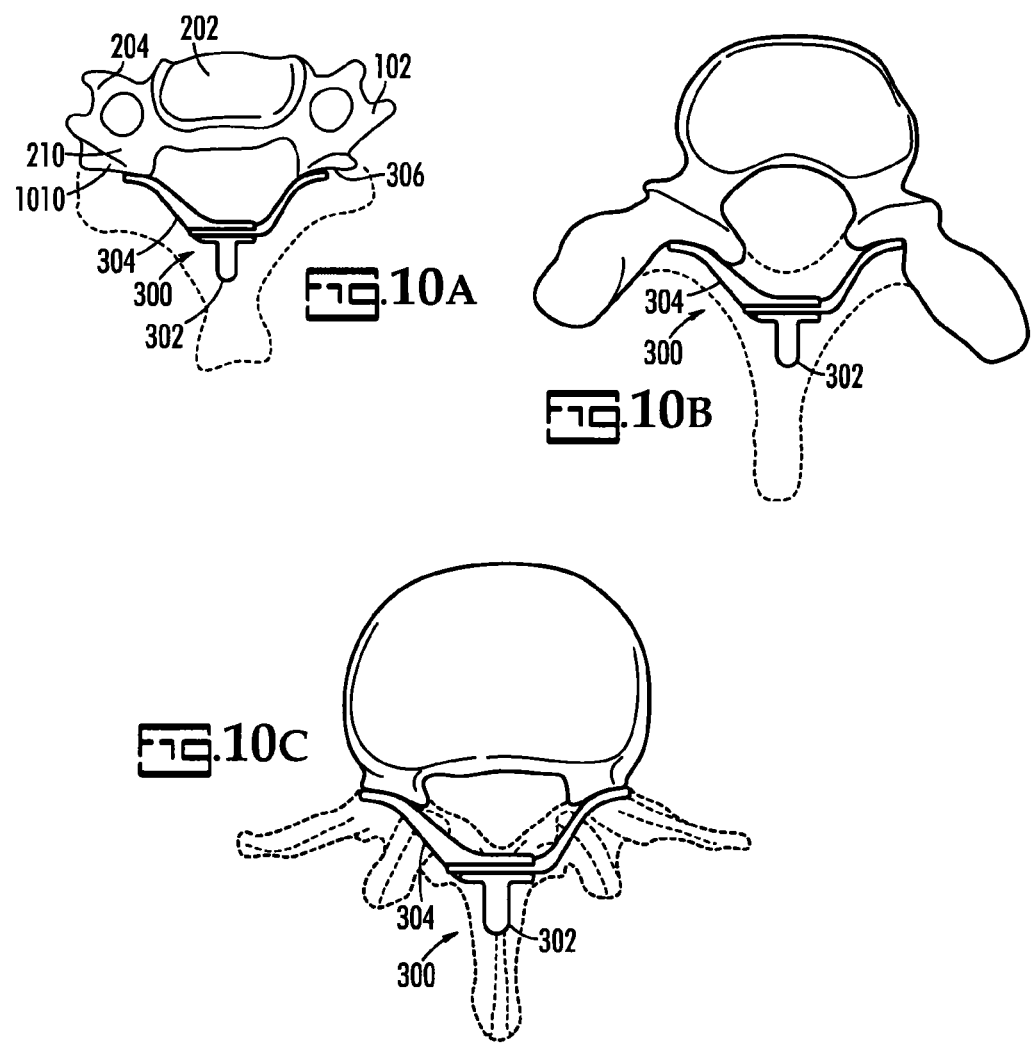

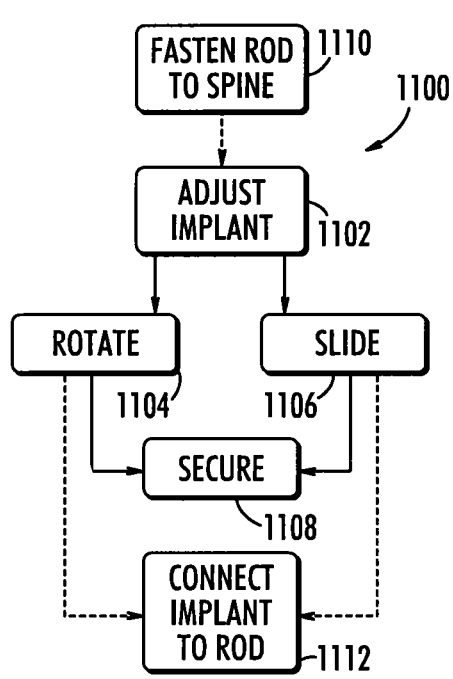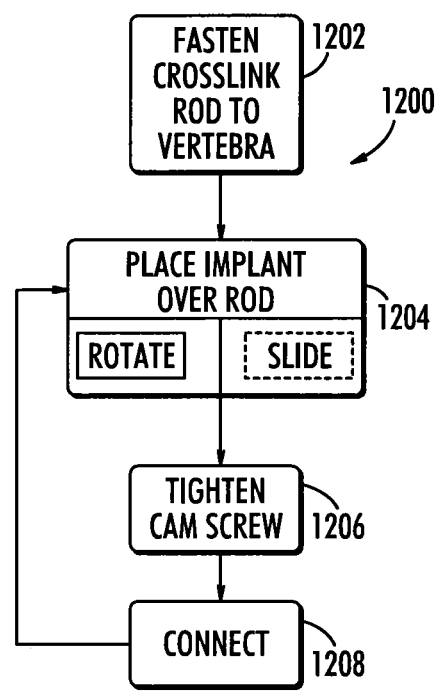

SPINAL IMPLANT APPARATUSES AND METHODS OF IMPLANTING AND USING SAME

RELATED APPLICATIONS

This application is related to an application entitled "Spring Screw Apparatuses and Methods of Using Same", filed on the same date of Dec. 17, 2010 in the United States Patent and Trademark Office, with the same named inventors, the disclosure of which is incorporated herein by reference.

FIELD AND BACKGROUND OF THE INVENTION

The present invention relates to spinal implants and methods of implantation and use of the implants in general, and more particularly to spinal implants for replacing at least the spinous process and/or for operating as cross-links and methods relating to same.

Referring to FIG. 1 a perspective view of the spinal anatomy is shown. Briefly, the spinal column 100 is divided into five sections beginning with the cervical section 102, the thoracic section 104, the lumbar section 106, the sacrum 108 and finally the coccyx 110. Each major section (cervical 102, thoracic 104, lumbar 106) is made up of individual bones called vertebrae. In a conventional spinal configuration, there are 7 cervical vertebrae, 12 thoracic vertebrae, and 5 lumbar vertebrae.

An individual vertebra is made up of several anatomical features. Generally, each vertebra of the three major sections has the same major features. FIG. 2 is a cross-sectional view of a thoracic vertebra 200. The body 202 of the vertebra is the primary area of weight bearing and provides a resting place for the fibrous discs which separate each of the vertebrae. The lamina 208 covers the spinal canal, the large opening in the center of the vertebra through which the spinal cord passes, and the neural foramen, where the spinal nerves exit. The spinous process 212 is the bone that can be felt when running a hand down a person's back. The paired transverse processes 204 are oriented 90 degrees to the spinous process 212 and provide attachment for back muscles. Pedicles 206 connect the transverse processes 204 to the body 202. Located between the transverse processes 204 and the laminae 208 are superior articular processes 210.

Often times, one or some of the major vertebral features is removed to effectuate treatment of a patient, for example in a laminectomy at least a portion of a lamina 208 is removed. It is not unusual for some or all of the spinous process 212, the laminae 208, the superior articular processes 210 or even the transverse processes 204 to be removed in a surgical procedure.

U.S. Pat. Nos. 7,566,345, 6,902,580 and 6,419,703 to Fallin, et al., the disclosures of which are incorporated herein by reference, describe prosthetic replacements for a posterior element of a vertebra comprising portions that replace the natural lamina and the four natural facets. The prosthetic replacements may also include portions that replace one or more of the natural spinous process and the two natural transverse processes. If desired, the prosthesis replacements may also replace the natural pedicles. Methods for replacing a posterior element of a vertebra are also provided.

United States Patent Application Publication No. US 2005/0033434 to Berry, the disclosure of which is incorporated herein by reference, describes a prosthetic device for interposition in a space left by one or more excised vertebral posterior structures. The prosthetic device comprises a lamina bridge having an inferior portion for replacing an excised lamina; at least one inferior facet replacement device, connected to the inferior portion of the lamina bridge, to replace an excised inferior articular process; and at least one superior facet replacement device to replace an excised superior articular process. The at least one superior facet replacement device articulates with the at least one inferior facet replacement device.

United States Patent Application Publication No. US 2005/0010291 to Stinson, et al., the disclosure of which is incorporated herein by reference, describes cephalad and caudal vertebral facet joint prostheses and methods of use. The cephalad prostheses are adapted and configured to be attached to a lamina portion of a vertebra without blocking a pedicle portion of the cephalad vertebra. In some embodiments, the prosthesis is attached with a non-invasive support member, such as a clamp. In other embodiments, a translaminar screw may be used for additional fixation.

PCT Application Publication No. WO 99/23963 to Senegas, the disclosure of which is incorporated herein by reference, describes a cervical vertebra implant comprising two branches adapted to extend respectively substantially along two cervical blades of a common cervical vertebra spaced from each other after osteotomy of the blades, and a rigid body linking the two branches.

SUMMARY OF THE INVENTION

An aspect of the present invention relates to providing a spinal implant device which is adjustable for adapting the implant to a variety of individual patient conditions and/or anatomies. In some embodiments of the invention, the implant is width adjustable by sliding at least a portion of the implant generally perpendicular to the spinal column to adjust the width of the implant to match the anatomical features of a particular vertebra. Additionally, optionally and/or alternatively, the spinal implant is orientation adjustable by rotating at least a portion of the implant around a vertical axis extending anteriorly/posteriorly as the patient is laying face down on a table. In some embodiments of the invention, the at least a portion of the implant that can be rotated is used to accommodate crosslink rods and/or to ease implantation. Optionally, rotation is used to attach the implant to non-parallel cross-link rods.

In an exemplary embodiment of the invention, the spinal implant is comprised of at least one of a prosthetic spinous process and/or at least one prosthetic lamina. In an embodiment of the invention, at least one hole is provided to the prosthetic spinous process for attachment of soft tissues, for example muscle.

In an embodiment of the invention, at least one loop is located on a lateral aspect of the prosthetic lamina. In an exemplary embodiment of the invention, at least one loop is used to secure the spinal implant to a vertebra by passing a screw therethrough and tightening the screw to a site on the vertebra, such as a lateral mass, facet, or pedicle.

In an embodiment of the invention, the spinal implant is adapted to be used with and/or as a part of a cross-link system. In some exemplary embodiments of the invention, the rod is a rod of a fusion construct or cross-linking system. By using a cam screw provided with a tapering cambered surface, the implant is secured to and/or accommodates different rod sizes (e.g. circumferences) without having to use a different screw and/or clamp for each possible size just by turning the screw until the taper of the cambered surface matches the size of the rod. In an embodiment of the invention, markings are provided to the screw and/or implant to indicate "open" and/or "closed" or "locked" and/or "unlocked" positions.

In an embodiment of the invention, the spinal implants, while adjustable, are offered in more than one size. For example, due to the differences in overall size between the cervical, thoracic and lumbar section of the spine, sizes tailored for these three sections of the spine are optionally offered, which are additionally adjustable for width as described elsewhere herein. In some embodiments of the invention, only two basic sizes are offered, thoracolumbar (thoracic and lumbar combined) and cervical.

A further aspect of the present invention relates to a cross-linking system including at least one of a spinal implant device and a cam screw provided with a tapered, cambered surface which is usable with a range of fusion rod sizes. In an embodiment of the invention, the spinal implant is provided with at least one screw hole to accommodate the insertion and/or rotation of the cam screw therein. In operation, with the cam screw inserted into the screw hole, a rotation tool interface end of the cam screw is positioned opposite a cam end of the screw such that the rotation tool interface end is accessible to an attending medical professional for applying rotational force, whereas the cam end is positioned proximal to a fusion rod secured to at least one vertebra.

In some embodiments of the invention, the spinal implant device is adjustable to a particular vertebra's anatomy. Optionally, the spinal implant is width adjustable. Optionally, additionally and/or alternatively, the spinal implant is orientation adjustable.

In an embodiment of the invention, a plurality of spinal implant devices are attached to the same at least one fusion rod to provide mechanical stability over a plurality of vertebrae. Optionally, at least two of the vertebrae are consecutive. Optionally, at least two of the vertebrae are not consecutive.

In an embodiment of the invention, the device is adapted to attach to a fusion rod at or near the spinous process. Optionally, the fusion rod at or around the spinous process is the third fusion rod attached to the device. In an embodiment of the invention, a plurality of fusion rod sizes are accommodated, for example by providing a cam screw, such as those described elsewhere herein to the spinous process for securing the rod in place. Optionally, a clamp-like mechanism is used to secure the rod to the device. Optionally, a tightening screw traps the rod against an immovable bracket to secure the rod. In some embodiments of the invention, the rod attached at or near the spinous process is attached in the same location on an adjacent implant, that is on an implant on a vertebra adjacent. Optionally, the rod is attached to an implant on a non-adjacent vertebra.

A further aspect of the present invention relates to a method of implanting a spinal implant by adjusting the spinal implant to adapt the implant to a particular patient's condition and/or anatomy. Optionally, adjusting includes sliding at least a portion of the implant to adapt. Optionally, adjusting includes rotating at least a portion of the implant to adapt. In an embodiment of the invention, the spinal implant is adjusted for width by sliding a portion of the implant to make the overall implant wider or narrower. In an embodiment of the invention, the spinal implant is adjusted for orientation by rotating at least a portion of the implant with respect to another portion of the implant.

A tightening screw is used to control the sliding portion of the implant from sliding relative to the non-sliding portion of the implant and/or to prohibit rotation of at least a portion of the implant with respect to another portion of the implant, in an embodiment of the invention. In an embodiment of the invention, control of the sliding and/or rotating is variable across a spectrum from moving freely to locked depending on the degree the screw is tightened. In an embodiment of the invention, the implant is fastened to a vertebra. Optionally, screws fasten the implant directly to a vertebra. The screws can be placed in a lateral mass, facet, lamina and/or pedicle of the bone, in an embodiment of the invention. Additionally, optionally and/or alternatively, the implant is connected to a cross-link apparatus wherein the cross-link apparatus is connected to at least one vertebra.

A further aspect of the present invention relates to a method of connecting a spinal implant device to at least one of a plurality of sizes of fusion rod. In an embodiment of the invention, at least one cross-link rod is attached to a plurality of vertebrae. Optionally, at least two of the vertebrae are consecutive. Optionally, at least two of the vertebrae are not consecutive.

In an embodiment of the invention, at least one spinal implant is placed over the pre-attached fusion rod using the adjustment features of the spinal implant, including sliding and/or rotating. In an embodiment of the invention, when the spinal implant is placed over the fusion rod, a cam screw which is provided to the spinal implant is in the "open" position, wherein the tapered, cambered surface of the cam screw is not yet engaged with the rod.

The spinal implant is connected to at least one fusion rod by tightening (i.e. rotating) the cam screw so that the tapered, cambered surface engages the rod. As the cam screw is turned in the tightening direction, the taper of the cambered surface gradually narrows. The cambered surface in contact with the rod therefore narrows as the cam screw is turned to accommodate rods of smaller and smaller circumference. In an embodiment of the invention, the cam screw is turned until the taper of the cambered surface matches the rod and the rod becomes immobilized between the cam screw and a bracket of the spinal implant. Optionally, the cam screw is rotated to a locked position.

In an embodiment of the invention, placing, tightening and connecting are repeated as necessary depending on the number of spinal implants being attached to the at least one fusion rod.

There is therefore provided in accordance with an embodiment of the invention, an adjustable spinal implant device, comprising: a sliding portion provided with a tongue; and, a non-sliding portion provided with a slot adapted for receipt of the tongue; wherein the tongue is slidably and rotatably positioned within the slot.

In an embodiment of the invention, a screw hole is provided to the non-sliding portion adapted for receipt of a tightening screw therein.

In an embodiment of the invention, the tightening screw defines an axis for rotation of the sliding and non-sliding portions with respect to each other.

In an embodiment of the invention, a sliding track located within the tongue is adapted for receipt of the tightening screw.

In an embodiment of the invention, the device further comprises a prosthetic spinous process. Optionally, the device further comprises at least one soft tissue attachment hole located on the prosthetic spinous process.

In an embodiment of the invention, the device further comprises at least one loop adapted for receipt of a bone screw therethrough on the anterior of at least one of the sliding portion and the non-sliding portion.

In an embodiment of the invention, the device further comprises at least one cam screw bracket adapted for receipt of a cam screw therethrough on the anterior of at least one of the sliding portion and the non-sliding portion. In some embodiments of the invention, the cam screw is provided with a cam retaining pin groove. Optionally, the cam retaining pin groove is provided with at least one locking point.

In an embodiment of the invention, the cam screw is provided with a tapered and cambered surface. Optionally, the tapered and cambered surface tapers from large to small in the tightening rotational direction. Optionally, the tapered and cambered surface is a counterpart to the outer circumference of a plurality of fusion rods.

In an embodiment of the invention, the spinal implant is between 20.0 mm to 45.0 mm in the anterior/posterior axis, between 10.0 mm to 30.0 mm in the superior/inferior axis, and between 25.0 mm to 55.0 mm in the dextro/sinistral axis. In some embodiments of the invention, the spinal implant is adapted for use with cervical vertebrae and is between 20.0 mm to 30.0 mm in the anterior/posterior axis, 10.0 mm to 20.0 mm in the superior/inferior axis and 25.0 mm to 35.0 mm in the dextro/sinistral axis. In some embodiments of the invention, spinal implant is adapted for use with thoracic vertebrae and is 25.0 mm to 35.0 mm in the anterior/posterior axis, 15.0 mm to 25.0 mm in the superior/inferior axis and 35.0 mm to 45.0 mm in the dextro/sinistral axis. In some embodiments of the invention, the spinal implant is adapted for use with lumbar vertebrae and is 35.0 mm to 45.0 mm in the anterior/posterior axis, 20.0 mm to 30.0 mm in the superior/inferior axis and 45.0 mm to 55.0 mm in the dextro/sinistral axis. In some embodiments of the invention, the spinal implant is adapted for use with the thoracolumbar section of the spine and is between 25.0 mm to 45.0 mm in the anterior/posterior axis, between 15.0 mm to 30.0 mm in the superior/inferior axis and between 35.0 mm to 55.0 mm in the dextro/sinistral axis.

In an embodiment of the invention, the implant is at least partially constructed of titanium.

In an embodiment of the invention, the implant is at least partially constructed of stainless steel.

In an embodiment of the invention, the implant is at least partially constructed of polyetheretherketone.

There is further provided in accordance with an exemplary embodiment of the invention, a cross-link system adapted for use with a plurality of fusion rod sizes, comprising: at least one fusion rod; at least one spinal implant provided with at least one bracket located on the anterior of the implant; and, at least one cam screw inserted through the at least one bracket and provided with a tapered and cambered surface wherein the cambered surface tapers across a spectrum corresponding to a plurality of outer circumferences of a plurality of fusion rods.

In an embodiment of the invention, the cambered surface is adapted to selectively trap the at least one fusion rod between the cam screw and the bracket.

In an embodiment of the invention, the at least one spinal implant is provided with two portions which are slidable and rotatable in relation to each other to assist with positioning the cam screw against the at least one fusion rod.

In an embodiment of the invention, the taper of the cambered surface narrows in the tightening rotational direction.

In an embodiment of the invention, the plurality of outer circumferences of a plurality of fusion rods ranges from 3.3 mm to 5.0 mm.

There is further provided in accordance with an exemplary embodiment of the invention, a locking cam screw, comprising, a cambered surface on a cam end; and, a retaining pin groove located around the circumference of a rotation tool interface end opposite the cam end on the cam screw; wherein the retaining pin groove is provided with at least one locking point adapted to pass a retaining pin therethrough in at least a tightening direction.

In an embodiment of the invention, the at least one locking point is a narrowing of the retaining pin groove.

In an embodiment of the invention, the position of the at least one locking point in the retaining pin groove relates to the rotational distance of cam screw needed to match the cambered surface to the outer circumference of a cross-link rod In an embodiment of the invention, the retaining pin groove is provided with a plurality of locking points. In some embodiments of the invention, each of the plurality of locking points corresponds to a rotational distance needed to match the cambered surface to an outer circumference of a cross-link rod.

There is further provided in accordance with an exemplary embodiment of the invention, a method for implanting a spinal implant at an implant site, comprising: adjusting the spinal implant to the implant site by at least one of sliding and rotating at least a first portion with respect to a second portion of the implant; and, securing the spinal implant to the implant site.

In an embodiment of the invention, the method further comprises fastening at least one cross-link rod so that is traverses the implant site. In some embodiments of the invention, the method further comprises connecting the implant to the at least one cross-link rod.

In an embodiment of the invention, the implant site includes at least one of a pedicle, a facet, a lateral mass and a lamina.

In an embodiment of the invention, the method further comprises tightening a screw to selectively limit at least one of sliding and rotating.

There is further provided in accordance with an exemplary embodiment of the invention, a method for connecting at least one spinal implant to at least one of a plurality of cross-link rods in a cross-link arrangement, comprising: connecting at least one cross-link rod to a plurality of vertebrae; placing at least one spinal implant over the at least one cross-link rod wherein a cambered surface of a cam screw provided to the spinal implant is in the open position and proximal to the cross-link rod; and, tightening the cambered and tapered cam screw so that it engages the cross-link rod and pins it between the cam screw and the spinal implant.

In an embodiment of the invention, the method further comprises repeating placing and tightening for additional spinal implants and cross-link rods.

In an embodiment of the invention, the placing includes at least one of sliding and rotating at least a portion of the spinal implant.

In an embodiment of the invention, the wherein at least two consecutive vertebrae are connected.

In an embodiment of the invention, the at least two non-consecutive vertebrae are connected.

In an embodiment of the invention, the method further comprises locking the cam screw to inhibit back rotation of the cam screw.

These and other features and their advantages will be readily apparent to those skilled in the art of spinal implants from a careful reading of the Detailed Description of Exemplary Embodiments, accompanied by the following drawings.

BRIEF DESCRIPTION OF THE DRAWINGS

Embodiments of the invention are herein described, by way of example only, with reference to the accompanying drawings. In this regard, the description taken along with the drawings makes apparent to those skilled in the art how embodiments of the invention may be practiced. It should also be understood that drawings may not be to scale. In the figures, FIG. 1 is a perspective view of the spinal anatomy;

FIG. 2 is a cross-sectional view of a lumbar vertebra;

FIG. 7A is a perspective view of an implant with a cam screw arrangement for interfacing with a rod of a cross-link system, in accordance with an exemplary embodiment of the invention;

FIG. 7B is a side view of the implant of FIG. 7A showing where the cross-sectional view of FIG. 7C is taken from, in accordance with an exemplary embodiment of the invention;

FIG. 7C is a cross-sectional view of the implant of FIG. 7A, in accordance with an exemplary embodiment of the invention;

FIG. 8 is a perspective view of a cam screw used in a cam screw arrangement for interfacing with a rod of a cross-link system, in accordance with an exemplary embodiment of the invention;

FIG. 9A is a side view of an altered spinal column with a spinal implant implanted thereon, in accordance with an exemplary embodiment of the invention;

FIG. 9B is a side view of an altered spinal column with a cross-linked spinal implants implanted thereon, in accordance with an exemplary embodiment of the invention;

FIGS. 10A-C are cross-sectional views of altered cervical, thoracic and lumbar vertebrae, respectively, with a spinal implant implanted thereon, in accordance with an exemplary embodiment of the invention;

FIG. 11 is a flowchart showing a method of implanting a spinal implant, in accordance with an exemplary embodiment of the invention; and, FIG. 12 is a flowchart showing a method for attaching a spinal implant to any one of a plurality of fusion rod sizes, in accordance with an exemplary embodiment of the invention.

DETAILED DESCRIPTION OF EXEMPLARY EMBODIMENTS

Figure 3A:
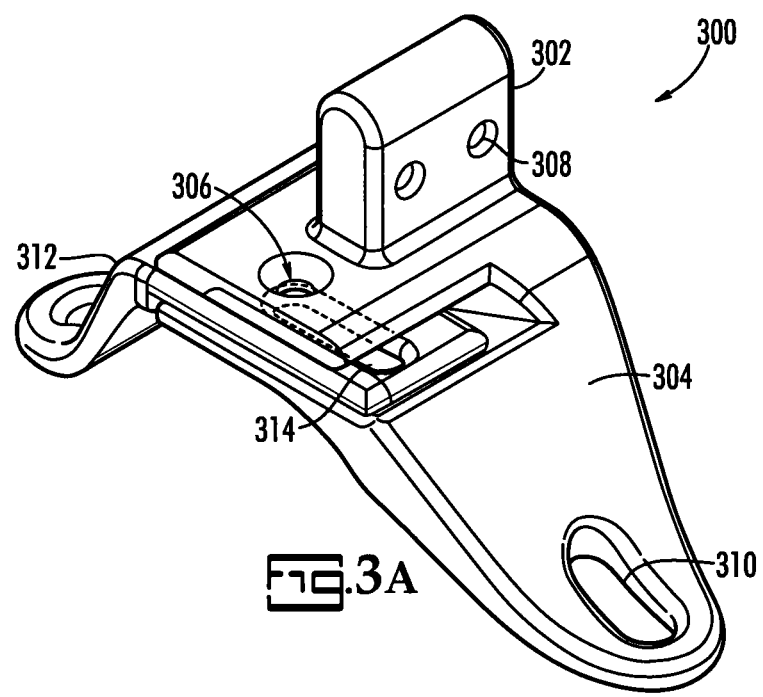
FIG. 3A is a perspective view of a sliding spinal implant with a prosthetic spinous process in a narrow configuration, in accordance with an exemplary embodiment of the invention.

Exemplary embodiments of spinal implants are described herein. In some embodiments of the invention, spinal implants are used to reconstruct damaged and/or defective spinal structures, particularly the spinous process and/or the laminae. In an embodiment of the invention, a spinal implant is used as a prosthesis for vertebrae in any, some or all of the cervical 102, thoracic 104, lumbar 106 or sacral 108 sections of the spinal column 100. Additionally, alternatively and/or optionally, a spinal implant is used as a component in a cross-link system for linking two or more vertebrae together, in an embodiment of the invention.

In an embodiment of the invention, spinal implant 300 is offered in a plurality of configurations adapted for use in the cervical 102, thoracic 104, and/or lumbar 106 sections of the spine. Optionally, a single configuration is adapted for use with both the thoracic and lumbar sections. Optionally, at least one of the configurations is offered in a plurality of sizes, for example the thoracolumbar configuration could be offered in a "large", "medium" and/or a "small" size. In an embodiment of the invention, an implant is sized for use by altering the dimensions in the anterior/posterior axis ("depth"), the super/inferior axis ("height") and/or the dextro/sinistral ("width") axis. For example, spinal implants described herein are sized between 20.0 mm to 45.0 mm in the anterior/posterior axis, in an embodiment of the invention. Spinal implants described herein are sized 10.0 mm to 30.0 mm in the superior/inferior axis, in some embodiments of the invention. In some embodiments of the invention, spinal implants described herein are sized between 25.0 mm to 55.0 mm in the dextro/sinistral axis. It should be understood that these numbers are by way of example only and that sizes and/or dimensions given herein are not necessarily those of every embodiment.

In an embodiment of the invention, the spinal implant adapted for use with the cervical section of the spine is approximately 20.0 mm to 30.0 mm in depth (from anterior to posterior when the device is implanted), 10.0 mm to 20.0 mm in height (from superior to inferior when the device is implanted) and 25.0 to 35.0 mm in width in the dextro/sinistral axis.

In an embodiment of the invention, the spinal implant adapted for use with the thoracic section of the spine is approximately 25.0 mm to 35.0 mm in depth, 15.0 mm to 25.0 mm in height and 35.0 mm to 45.0 mm in width.

In some embodiments of the invention, a spinal implant adapted for use with the lumbar section of the spine is approximately 35.0 mm to 45.0 mm in depth, 20.0 mm to 30.0 mm in height and 45.0 mm to 55.0 mm in width.

As described above, a single size and/or configuration could be used with the thoracolumbar section of the spine. These sizes would be in the range of 25.0 mm to 45.0 mm in depth; 15.0 mm to 30.0 mm in height, and 35.0 mm to 55.0 mm in width, in an exemplary embodiment of the invention.

Figure 3B:
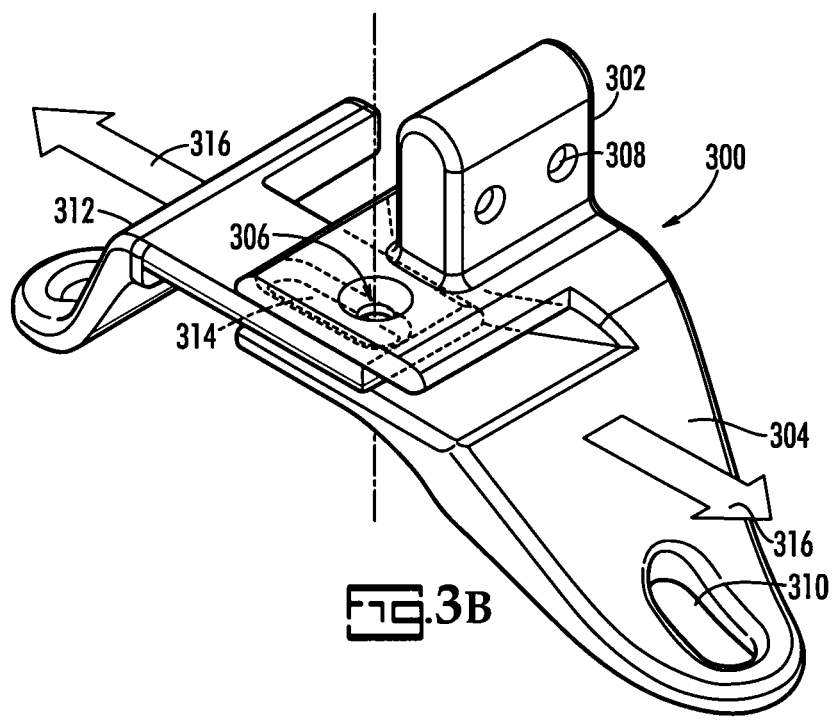
FIG. 3B is a perspective view of a sliding spinal implant with a prosthetic spinous process in at least a partially open or wide configuration, in accordance with an exemplary embodiment of the invention.

In an embodiment of the invention, the spinal implant is width adjustable by using a slidable portion of the implant, for example as shown and described with respect to FIGS. 3A and 3B, inter alia. Optionally, opposing components of the spinal implant are rotatable around a vertical axis (from the perspective of the attending medical professional when the patient is laying face down) extending in the anterior/posterior axis of the implant, for example as shown and described with respect to FIGS. 4, and 5A-5C, inter alia.

Another feature of some embodiments of the invention relates to a plurality of interchangeable anterior portions which are used for connecting the spinal implants to vertebrae and/or in a cross-linking arrangement. Nearly all of the Figures show at least one embodiment for connection, including loops (FIGS. 3A-3B, 4, 5A-5B), or brackets with a cam screw (FIGS. 6, 7A-7C). It should be understood that some or all of these connection embodiments are adapted for use with any of the spinal implants described herein and vice versa.

Referring to FIGS. 3A and 3B, in some embodiments of the invention, a non-sliding portion 304 and a sliding portion 312 are adapted to simulate and/or replace the natural laminae 208 of the vertebra 200, in an embodiment of the invention. In some exemplary embodiments of the invention, non-sliding portion 304 and sliding portion 312 also replace the natural superior articular processes 210 extending from the prosthetic spinous process 302 to the transverse process 204 and/or the pedicle 206. In an embodiment of the invention, non-sliding portion 304 and/or sliding portion 312 are adapted to provide more clearance between spinal implant 300 and the spinal cord and/or thecal sac (in the case of the lumbar section) located within the spinal column 100. For example, non-sliding portion 304 and/or sliding portion 312 are arched at least as much as the natural portions of the vertebra being replaced. Optionally, non-sliding portion 304 and/or sliding portion 312 are arched more than the natural portions of the vertebra being replaced.

Spinal implant 300 is constructed of any material which is biocompatible and which is mechanically capable of withstanding stresses of cross-linking, for those embodiments of the invention which are used in a cross-linking arrangement. In some embodiments of the invention, spinal implant 300 is constructed of a metal, for example titanium. In some exemplary embodiments of the invention, spinal implant 300 is constructed of a polymer material, for example polyetheretherketone (PEEK). In an embodiment of the invention, the implant is constructed from any bio-compatible material rigid enough to function as at least a portion of a prosthetic lamina and/or spinous process and/or in a cross-link system.

Spinal implant 300 is intended to be adaptable to a variety of patient conditions and/or anatomies so that less device sizes are required to be on hand and/or manufactured in order to suit an individual patient's needs. In some embodiments of the invention, at least a portion of the spinal implant slides with respect at least another portion of the implant in order to adjust the overall width (as used above in paragraph with respect to "width") of the implant allowing the implant to be adaptable to a variety of patient conditions and/or anatomies. FIG. 3A shows a perspective view of a sliding spinal implant 300 with a prosthetic spinous process 302 in a narrow configuration, in accordance with an exemplary embodiment of the invention. That is, in its narrowest configuration whereby the sliding portion 312 and the non-sliding portion 304 abut one another to create a configuration of the narrowest achievable width for implant 300. FIG. 3B, however, shows implant 300 at least partially "open" or wider by taking advantage of the sliding feature of the sliding portion 312 and the non-sliding portion 304 counterparts in the direction of arrows 316. It should be understood that implant width is also adjustable when rotated, as described below in more detail with respect to FIGS. 4, and 5A-5C.

In an embodiment of the invention, sliding portion 312 slides with respect to non-sliding portion 304 of spinal implant 300 in order to increase and/or decrease the overall width of spinal implant 300. It is noted that "non-sliding" portion is used for nomenclature only and that in practice it is possible that sliding portion 312 remains still while non-sliding portion 304 slides towards or away from sliding portion 312, or they both 304, 312 slide simultaneously. At least one screw hole 306 is provided to spinal implant 300 which enables a tightening screw (not pictured) to be used to lock the spinal implant 300 width once the desired width is achieved by sliding. In an embodiment of the invention, sliding portion 312 is provided with a tongue 318 which is adapted to be slidable within a slot 320 formed by non-sliding portion 304 for width adjustment. In an embodiment of the invention, a track 314 is located on tongue 318 of sliding portion 312 to accommodate the tightening screw along a range of lengths of spinal implant 300.

In some embodiments of the invention, the slide adjustable implant 300 is adjustable by hand. In an embodiment of the invention, the sliding action of the sliding portion 312 and/or non-sliding portion 304 with respect to each other is controllable across a spectrum from sliding freely to locked by the tightening screw which when fully tightened stops the sliding portion from sliding relative to the non-sliding portion of the implant. Optionally, at least the sliding portion 312 is demarcated for precise and/or accurate adjustment of the implant. For example, the sliding portion 312 is marked with pre-selected position numbers and/or an actual distance measurement indication. In an embodiment of the invention, the slide of the sliding portion 312 is located near or at the intersection of the spinous process 302 (or where the spinous process would normally be) and the laminae. In some embodiments of the invention, sliding portion 312 is located on the spinous process 302 on the posterior side of the implant 300.

Figure 4:
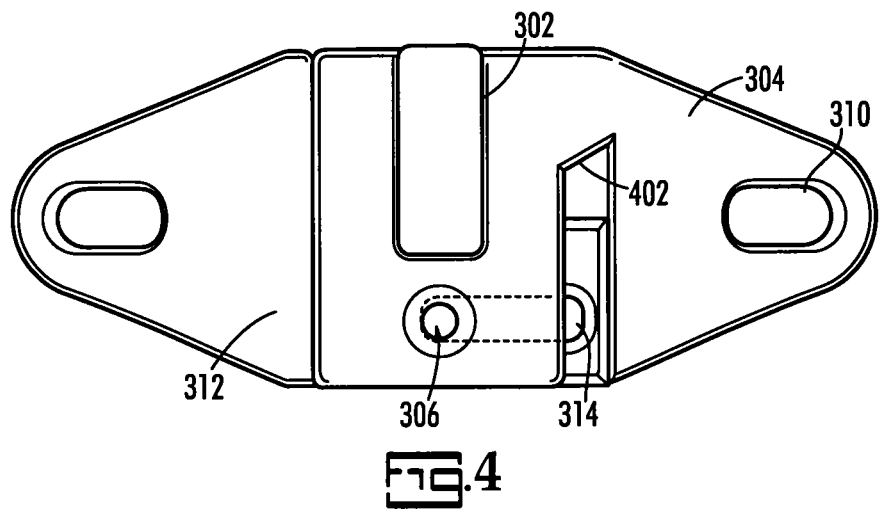
FIG. 4 is a top view of a sliding spinal implant with a prosthetic spinous process, in accordance with an exemplary embodiment of the invention.

Screw hole 306 and track 314 are more clearly seen in FIG. 4, a top view of sliding spinal implant 300 with a prosthetic spinous process 302, in accordance with an exemplary embodiment of the invention. In an embodiment of the invention, the prosthetic spinous process 302 has located therein at least one hole 308 for attachment of soft tissues, for example muscle. In an embodiment of the invention, at least one loop 310 is provided to spinal implant 300 which is adapted for receipt of a pedicle and/or lateral mass screw therethrough. Optionally, the at least one loop 310 is adapted for use with a spring screw as described in related application entitled Spring Screw Apparatus and Methods of Using same, filed on the same date as this application. In some embodiments of the invention, at least one loop 310 is located on the anterior portion (anatomically speaking) of spinal implant 300. In an embodiment of the invention, locating loops 310 anteriorly allows for spinal implant 300 to be attached to the spinal column through the loop 310.

Also visible in FIG. 4 is at least a part of the rotation wedge 402 located on the non-sliding portion 304. Rotation wedge 402 is shown and described in more detail with respect to FIGS. 5A-5C. Non-sliding portion 304 is adapted with rotation wedge 402 to allow rotation of the sliding portion 312 and the non-sliding portion 304 with respect to each other.

Figure 5A:
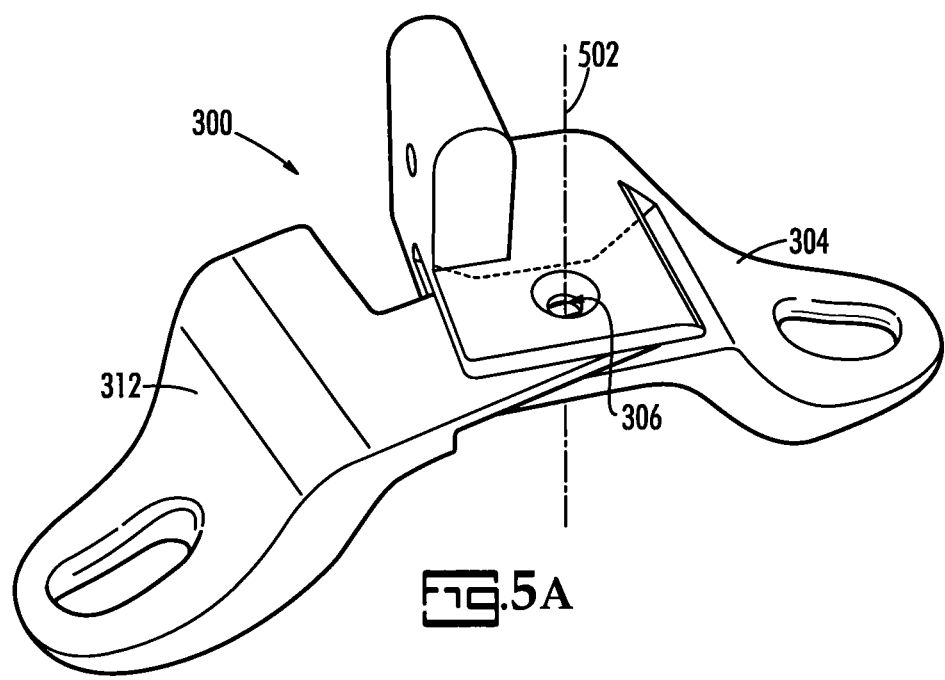
FIG. 5A is a perspective view of a spinal implant with opposing components rotating about a vertical axis, in accordance with an exemplary embodiment of the invention.

FIG. 5A is a perspective view of spinal implant 300 with opposing components 304, 312 rotating about a vertical axis 502, in accordance with an exemplary embodiment of the invention. In an embodiment of the invention, implant 300 is adjustable not only in width as described above but also in orientation whereby implant 300 is provided at least a second degree of motion around vertical axis 502 (the first degree being the adjustable width) to accommodate for variations in spinal anatomy from patient to patient and/or from vertebra to vertebra. A screw or pin is nominally inserted into screw hole 306 mechanically defining the vertical axis 502 about which rotation occurs. In use, the screw or pin is also used to secure the implant 300 configuration for width and/or for rotation, for example by screwing down to tighten the connection between components 304, 312 and/or eventually prohibiting relative movement between the two. Optionally, the securing is not permanent but temporary, for example if adjustments need to be made to width and/or rotation at a later date.

Figure 5B:
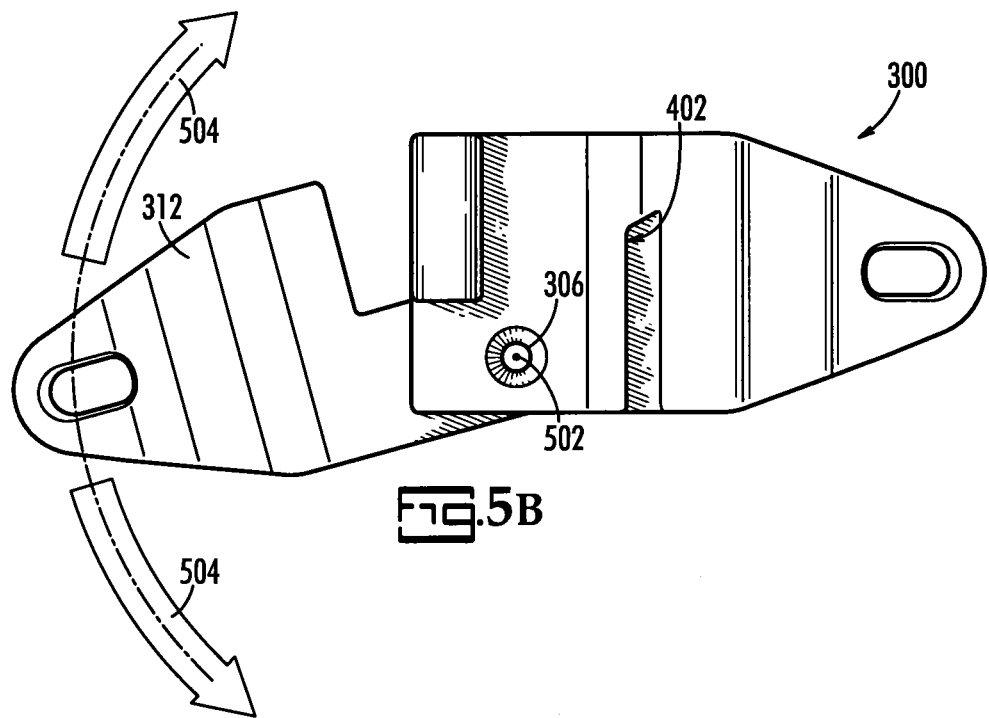
FIG. 5B is a top view of a spinal implant with opposing components rotating about a vertical axis, in accordance with an exemplary embodiment of the invention.

FIG. 5B is a top view of a spinal implant with opposing components 304, 312 rotating about vertical axis 502, in accordance with an exemplary embodiment of the invention.

Rotation about vertical axis 502 provides an additional degree of freedom, shown by rotational motion arrows 504 to implant 300. It can be seen that by rotating implant 300 it can be implanted on an asymmetrical vertebra, for example where the excision of parts of the vertebra results in an asymmetrical implantation site for implant 300, in an embodiment of the invention.

Figure 5C:
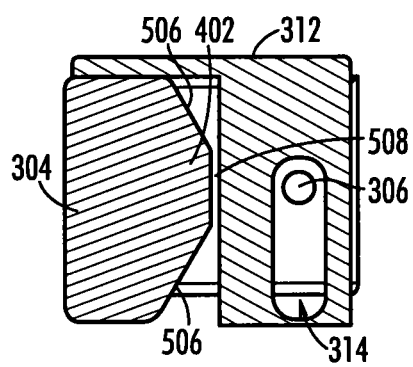
FIG. 5C is a cross-sectional view of a portion of a spinal implant with opposing components capable of rotating about a vertical axis, in accordance with an exemplary embodiment of the invention.

FIG. 5C is a cross-sectional view of rotation wedge 402 of a spinal implant 300 with opposing components 304, 312 capable of rotating about a vertical axis 502, in accordance with an exemplary embodiment of the invention. Rotation wedge 402 is a part of non-sliding portion 304, in an embodiment of the invention. Wedge 402 is provided with angled faces 506 which set the maximum rotational angle at which sliding portion 312 can rotate with respect to non-sliding portion 304. In an embodiment of the invention, the maximum rotational angle up to 90 degrees. Optionally, the maximum rotational angle is up to 30 degrees. In an embodiment of the invention, a non-angled face 508 is provided to non-sliding portion 504 to provide a base, non-rotated configuration for implant 300.

Figure 6:
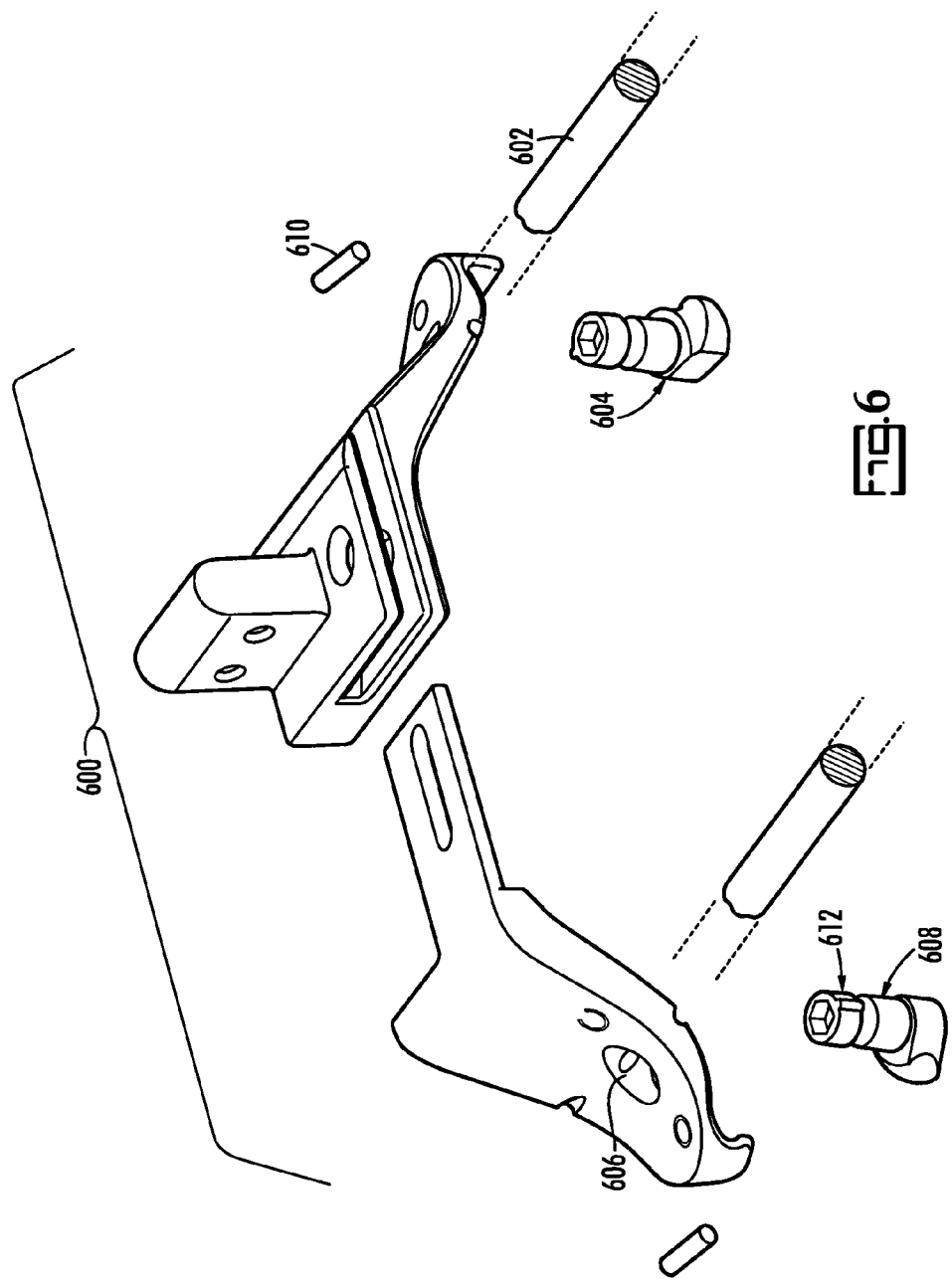
FIG. 6 is an exploded view of a spinal implant with a cam screw arrangement for interfacing with at least one rod of a spinal implant system, in accordance with an exemplary embodiment of the invention.

FIG. 6 is an exploded view of a spinal implant 600 with a cam screw arrangement for interfacing with at least one rod 602 of a spinal implant system, in accordance with an exemplary embodiment of the invention. As described elsewhere herein, spinal implants 300, 600 are used as prosthetics to stand in for excised, altered, and/or damaged portions of the spinal column. Additionally and/or optionally and/or alternatively, spinal implants described herein are used as at least a part of a cross-linking system for stabilizing at least a portion of the spine by mechanically linking two or more vertebrae together. In an embodiment of the invention, at least one cam screw 604 is provided to implant 600 which in nominal operation is rotatably positioned within a screw hole 606. Screw hole 606 and cam screw 604 are relatively sized to permit the rotation of cam screw 604 within screw hole 606, but to prevent the passage of the cam end 608 of cam screw 604 from passing through screw hole 606. In an embodiment of the invention, a cam retaining pin 610 is used to prevent the rotation tool interface end 612 of cam screw 604 from passing through the screw hole 606 and/or to provide a locking mechanism for the cam screw arrangement. The cam screw arrangement is described in more detail with respect to FIGS. 7A-7C and 8.

In an embodiment of the invention, the implant 300, 600 is adapted to attach to a fusion rod at or near the spinous process. Optionally, the fusion rod at or around the spinous process 302 is the third fusion rod attached to the device. In an embodiment of the invention, a plurality of fusion rod sizes are accommodated, for example by providing a cam screw, such as those described elsewhere herein to the spinous process 302 for securing the rod in place. Optionally, a clamp-like mechanism is used to secure the rod to the device. Optionally, a tightening screw traps the rod against an immovable bracket to secure the rod. In some embodiments of the invention, the rod attached at or near the spinous process is attached in the same location on an adjacent implant, that is on an implant on a vertebra adjacent. Optionally, the rod is attached to an implant on a non-adjacent vertebra.

FIG. 7A is a perspective view of implant 600 with a cam screw arrangement for interfacing with a rod 602 of a cross-link system, in accordance with an exemplary embodiment of the invention. The cam screw arrangement features the ability to connect implant 600 to a plurality of different sized (e.g. circumference) rods 602 by providing a cambered surface 702 on the cam end 608 of cam screw 604 which gradually reduces/increases (depending on direction of motion) in size across the range of motion of the screw 604, in accordance with an embodiment of the invention. Starting at the largest portion of the cambered surface 702, the screw 604 is tightened until the rod 602 is securely connected to the implant 600, being trapped between the cam screw 604 and the bracket portion 708 of the implant 600, allowing for rods 602 to be used with implant 600 which go from as large as the largest part of the cambered surface 702 to as small as the smallest part of the cambered surface 702. Optionally, the rod is tightened in a clockwise direction. In some embodiments of the invention, size markings are provided on the implant 600 and/or screw 604 to show to the attending medical professional how much the screw 604 needs to be turned to properly secure the rod 602 being used to the implant 600.

FIG. 7C is a cross-sectional view of implant 600, taken from the cross-section indicated in FIG. 7B, with a cam screw arrangement for interfacing with a rod 602 of a cross-link system, in accordance with an exemplary embodiment of the invention. Seen in greater detail is the positioning of fusion rod 602 with respect to cam screw 604, wherein the cambered surface 702 acts as a counterpart to the rod 602. Also shown in greater detail is cam retaining pin 610, which in an embodiment of the invention is located at least partially within a retaining pin groove 704. Retaining pin groove 704 and cam retaining pin 610 are adapted to provide at least one of the functions of mechanically preventing end 612 from passing through screw hole 606 and providing a locking mechanism to the cam screw arrangement. In an embodiment of the invention, cam retaining pin 610 is rigid. In an embodiment of the invention, the retaining pin groove 704 extends around the circumference of rotation tool interface end 612.

In an embodiment of the invention, the cam retaining pin is provided with clearance from the cam screw so that the cam screw can rotate freely but is still prevent from passing through screw hole 606.

The locking mechanism function is provided by adapting retaining pin groove 704 with a locking point 706 which is sized and shaped so that as the cam screw 604 is intentionally rotated, the retaining pin 610 is impinged and/or crossed over the locking point 706 whereby once on the other side of the locking point 706 back rotation of the cam screw 604 is inhibited, absent intentional back rotational force applied to the cam screw 604.

In an embodiment of the invention, the cam retaining pin is positioned to interface with the cam retaining groove. Optionally, the retaining pin groove 704 is provided with a plurality of locking points, serially arranged in the groove 704. Additionally and/or optionally, the locking points are located in the retaining pin groove 704 to correspond to commercially available and/or commonly used rod sizes such that at least one locking point is provided for each size. In an embodiment of the invention, as the cam screw 604 is turned it "locks" repetitively where back rotation is inhibited up to and including the final locking when the cambered surface 702 size matches the rod size and wherein the locking point placed in the retaining pin groove to match that rod size is traversed.

In an embodiment of the invention the cam retaining pin 610 is flexible. Optionally, the cam retaining pin 610 is constructed of rubber, stainless steel, or a polymer, for example PEEK. In some embodiments of the invention, the polymer is biodegradable. Optionally, the polymer is non-biodegradable.

It should be noted that in an embodiment of the invention, fusion rods which are not perfectly parallel, as attached to the patient's spine, can still be used in conjunction with the implants described herein which have the width and/or orientation adapting features. Non-parallel rods will increase or decrease distance from each other at a set angle as you move up or down the spine. By using the adjustable width and/or the adjustable orientation features of the implants described herein, a single implant model can be used, rather than having a plurality of individually specialized implants designed to accommodate non-parallel rods.

The spinal implants described herein 300, 600 also accommodate for size differences amongst individual vertebral segments, in an embodiment of the invention. For instance, size variability within the cervical spine. A feature of implant 600 relative to its configuration is that as a cross-link, its generally triangular geometry reduces the risk of impingement on the spinal cord and/or thecal sac. This is contrast to existing cross-links which are straight, wherein there is a risk of impingement. Therefore, the traditional cross-links cannot always be used. It is noted that other spinal implants described herein also possess triangular geometry.

FIG. 8 is a perspective view of cam screw 604 used in a cam screw arrangement for interfacing with rod 602 of a cross-link system, in accordance with an exemplary embodiment of the invention. Shown in more detail is the cambered surface 702 of cam screw, as well as the retaining pin groove 704, which in this figure does not show any locking points 706. Optionally, no locking points 706 are used.

In an embodiment of the invention, the cambered surface 702 of the cam screw is adapted to interface with commonly used rod sizes, for example ranging from 3.3 mm to 5.0 mm. It should be understood, however, that the cam screw could be adapted with a camber to match almost any rod size which is usable for a cross-linking system.

In an embodiment of the invention, spinal implant 300, 600 is adapted to be used with a spring screw, for example as described in related patent application entitled Spring Screw Apparatus and Methods of Using Same, filed on the same date as this application. Spinal implant 300 is provided with a flange around the at least one loop 310 which acts as a counterpart to a spring located on the screw to lock the spring in the plane of the flange such that as the spring screw is tightened the implant 300 tightens to the vertebra.

FIG. 9A is a perspective view of a damaged spinal column 100 with a spinal implant 300, 600 implanted thereon, in accordance with an exemplary embodiment of the invention. It can be seen that a plurality of spinal implants 300, 600 on consecutive vertebrae can be cross-linked, shown in FIG. 9B and as described herein, in some exemplary embodiments of the invention.

FIG. 10A is a cross-sectional view of a modified cervical vertebra 1002 with spinal implant 300 implanted thereon, in accordance with an exemplary embodiment of the invention. In the exemplary embodiment shows, implant 300 is attached to a vertebra 1002 at the inferior articular process 1010 and functions as a lamina prosthetic. It should be understood with respect to FIG. 10A and FIGS. 10B-10C below, that depending on the condition of the patient different parts of the vertebra may need to be replaced and therefore, implant 300 is attached accordingly. For example, in an embodiment of the invention, implant 300 is attached to the vertebra at the pedicles. In some embodiments of the invention, implant 300 is attached at a facet or what is left of a lamina after a partial laminectomy. In some embodiments of the invention, one side of the implant is attached to a different anatomical part than the other side of the implant or at a different corresponding location on the same anatomical part.

FIG. 10B is a cross-sectional view of a modified thoracic vertebra 1004 with spinal implant 300 implanted thereon, in accordance with an exemplary embodiment of the invention.

FIG. 10C is a cross-sectional view of a modified lumbar vertebra 1006 with spinal implant 300 implanted thereon, in accordance with an exemplary embodiment of the invention.

FIG. 11 is a flowchart 1100 showing a method of implanting spinal implant 300, 600 at an implant site, in accordance with an exemplary embodiment of the invention. Spinal implant 300, 600 is adjusted (1102) to fit a specific vertebral anatomy at an implant site and/or for use in a cross-linking arrangement over a plurality of vertebrae by an attending medical professional who is either performing or assisting the performance of the implantation procedure, in an embodiment of the invention. In an embodiment of the invention, spinal implant 300, 600 is adjusted by rotating (1104) and/or sliding (1106) at least a portion of the implant with respect to another portion of the implant such that the desired length and/or orientation of the implant is achieved. In an embodiment of the invention, control of the sliding and/or rotating is selectively variable across a spectrum from moving freely to locked depending on the degree the screw is tightened.

In an embodiment of the invention, screws are passed through the loops 306 and screwed at the fastening locations into the vertebra 200 to secure (1108) spinal implant 300, 600. The screws can be placed in a lateral mass, facet, lamina and/or pedicle of the bone, in an embodiment of the invention.

In some embodiments of the invention, spinal implant 300 is connected and/or is a component of a cross-linking system whereby the implant is connected to at least one rod 602 which is in turn connected to at least one vertebra such that the rod traverses the implant site. In an embodiment of the invention, at least one cross-link rod is fastened (1110) to the spine and then at least one spinal implant is connected (1112) to the rod. Alternatively, the implant is connected first to the rod and then the rod is fastened to the spine.

FIG. 12 is a flowchart 1200 showing a method for enabling attachment of a spinal implant 600 to a plurality of different sized cross-link rods, in accordance with an exemplary embodiment of the invention. In an embodiment of the invention, the fusion rod 602 is fastened (1202) to at least one vertebra. In an embodiment of the invention, fastening (1202) is performed in any one of the known methodologies. At least one spinal implant 600 is placed (1204) over the rod 602 such that bracket 708 receives the rod 602 between the bracket 708 and the cam screw 604. In an embodiment of the invention, at least one spinal implant is placed (1204) over the pre-attached cross-link rod using the adjustment features of the spinal implant, including sliding and/or rotating. In an embodiment of the invention, when the spinal implant is placed (1204) over the cross-link rod, the cam screw 604 which is provided to the spinal implant is in an "open" position, wherein the cambered surface 702 of the cam screw 604 is not yet engaged with the rod 602.

In an embodiment of the invention, placement (1204) of the implant 600 includes adjusting the implant 600 width by sliding and/or adjusting the implant orientation by rotating, as described elsewhere herein.

The cam screw 604 is tightened (1206) until the rod 602 is securely connected (1208) to the spinal implant 600 by pinning the rod between the cam screw 604 and the bracket portion 708, in an embodiment of the invention. Optionally, connecting (1208) is enhanced by providing at least one locking position to the cam screw 604 such that as cam screw 604 is tightened (1206), cam retaining pin 610 traverses a protrusion in the retaining pin groove 704 which prevents back-rotation of the cam screw 604 (establishing a "locking point"), absent intentionally applied back-driving force. Optionally, the locking position is adapted to correspond to a specific cross-link rod size, for example one that is popularly used and/or readily commercially available. In some embodiments of the invention, where a plurality of locking positions are provided to cam screw 604 retaining pin groove 704, the cam screw 604 is tightened (1206) to the locking position which is closest to and/or which was specifically placed for the cross-link rod being connected (1208) to. Thus, in some embodiments of the invention, tightening (1206) includes traversing at least one locking point to arrive at the appropriately placed locking point for best fit. The process of attaching implants to the vertebrae for use in a cross-linking arrangement is repeated (1210) depending on how many vertebrae are being cross-linked together, in an exemplary embodiment of the invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Those familiar with spinal implants will appreciate that many modifications and substitutions can be made to the foregoing preferred embodiments of the present invention without departing from the spirit and scope of the present invention, defined by the appended claims.

What is claimed is:

1. An adjustable spinal implant device, comprising:
a sliding portion provided with a tongue;
a non-sliding portion provided with a slot adapted for receipt of the tongue and a screw hole adapted for receipt of a tightening screw therein, wherein the tongue is slidably and rotatably positionable within the slot; and
a cam screw configured to be inserted into one of the sliding portion and the non-sliding portion, the cam screw having a tapered surface that is of varying camber configured to match fusion rods of different sizes;
wherein the tightening screw defines an axis for rotation of the sliding and non-sliding portions with respect to each other.

2. An adjustable spinal implant device according to claim 1, further comprising at least one loop adapted for receipt of a bone screw therethrough on the anterior of at least one of the sliding portion and the non-sliding portion.

3. An adjustable spinal implant device according to claim 1, further comprising at least one cam screw bracket adapted for receipt of the cam screw therethrough on the anterior of at least one of the sliding portion and the non-sliding portion.

4. An adjustable spinal implant device according to claim 1, wherein the tapered surface tapers from large to small in the tightening rotational direction.

5. An adjustable spinal implant device according to claim 1, wherein the cam screw is provided with a cam retaining pin groove.

6. An adjustable spinal implant device according to claim 1, wherein the spinal implant is between 20.0 mm to 45.0 mm in the anterior/posterior axis, between 10.0 mm to 30.0 mm in the superior/inferior axis, and between 25.0 mm to 55.0 mm in the dextra/sinistral axis.

7. An adjustable spinal implant device according to claim 6, wherein the spinal implant is adapted for use with cervical vertebrae and is between 20.0 mm to 30.0 mm in the anterior/posterior axis, 10.0 mm to 20.0 mm in the superior/inferior axis and 25.0 mm to 35.0mm in the dextro/sinistral axis.

8. An adjustable spinal implant device according to claim 6, wherein the spinal implant is adapted for use with thoracic vertebrae and is 25.0 mm to 35.0 mm in the anterior/posterior axis, 15.0 mm to 25.0 mm in the superior/inferior axis and 35.0 mm to 45.0 mm in the dextra/sinistral axis.

9. An adjustable spinal implant device according to claim 6, wherein the spinal implant is adapted for use with lumbar vertebrae and is 35.0 mm to 45.0 mm in the anterior/posterior axis, 20.0 mm to 30.0 mm in the superior/inferior axis and 45.0 mm to 55.0 mm in the dextro/sinistral axis.

10. An adjustable spinal implant device according to claim 6, wherein the spinal implant is adapted for use with the thoracolumbar section of the spine and is between 25.0 mm to 45.0mm in the anterior/posterior axis, between 15.0 mm to 30.0 mm in the superior/inferior axis and between 35.0 mm to 55.0 mm in the dextro/sinistral axis.

11. An adjustable spinal implant according to claim 1, wherein the implant is at least partially constructed of titanium.

12. An adjustable implant according to claim 1, wherein the implant is at least partially constructed of stainless steel.

13. An adjustable spinal implant according to claim 1, wherein the implant is at least partially constructed of polyetheretherketone.

14. An adjustable spinal implant device according to claim 1, wherein a sliding track located within the tongue is adapted for receipt of the tightening screw.

15. An adjustable spinal implant device according to claim 1, further comprising a prosthetic spinous process.

16. An adjustable spinal implant device according to claim 15, further comprising at least one soft tissue attachment hole located on the prosthetic spinous process.

17. An adjustable spinal implant device according to claim 15, wherein the sliding portion and the non-sliding portion extend transversely from the prosthetic spinous process.

18. An adjustable spinal implant device according to claim 15, wherein the sliding portion and the non-sliding portion are arched at least as much as the natural portions of the vertebra being replaced.

19. An adjustable spinal implant device, comprising;
a sliding portion provided with a tongue;
a non-sliding portion provided with a slot adapted for receipt of the tongue and a screw hole adapted for receipt of a tightening screw therein, wherein the tongue is slidably and rotatably positionable within the slot and
a cam screw confiured to be inserted into one of the sliding portion and the non-sliding portion, the cam screw having a tapered surface that is of varying camber configured to match fusion rods of different sizes;
wherein a sliding track located within the tongue is adapted for receipt of the tightening screw.

20. An adjustable spinal implant device according to claim 19, wherein the tightening screw defines an axis for rotation of the sliding and non-sliding portions with respect to each other.

21. An adjustable spinal implant device according to claim 19, further comprising at least one cam screw bracket adapted for receipt of a cam screw therethrough on the anterior of at least one of the sliding portion and the non-sliding portion.

22. An adjustable spinal implant device according to claim 19, wherein the tapered and cambered surface tapers from large to small in the tightening rotational direction.

23. An adjustable spinal implant device according to claim 19, further comprising a prosthetic spinous process.

24. An adjustable spinal implant device according to claim 23, further comprising at least one soft tissue attachment hole located on the prosthetic spinous process.

25. An adjustable spinal implant device according to claim 23, wherein the sliding portion and the non-sliding portion extend transversely from the prosthetic spinous process.

26. An adjustable spinal implant device according to claim 23, wherein the sliding portion and the non-sliding portion are arched at least as much as the natural portions of the vertebra being replaced.

27. An adjustable implant device, comprising;
a sliding portion provided with a tongue;
a non-sliding portion provided with a slot adapted for receipt of the tongue, wherein the tongue is slidably and rotatably positionable within the slot; and
a cam screw confiured to be inserted into one of the sliding portion and the non-sliding portion, the cam screw having a tapered surface that is of varying camber configured to match fusion rods of different sizes;
wherein the cam screw is provided with a cam retaining pin groove that has at least one locking point.

28. An adjustable spinal implant device according to claim 27, wherein a screw hole is provided in the non-sliding portion adapted for receipt of a tightening screw therein.

29. An adjustable spinal implant device according to claim 27, further comprising a prosthetic spinous process.

30. An adjustable spinal implant device according to claim 29, further comprising at least one soft tissue attachment hole located on the prosthetic spinous process.

31. An adjustable spinal implant device according to claim 29, wherein the sliding portion and the non-sliding portion extend transversely from the prosthetic spinous process.

32. An adjustable spinal implant device according to claim 29, wherein the sliding portion and the non-sliding portion are arched at least as much as the natural portions of the vertebra being replaced.

33. An adjustable spinal implant device, comprising;
a sliding portion provided with a tongue;
a non-sliding portion provided with a slot adapted for receipt of the tongue, wherein the tongue is slidabl and rotatably positionable within the slot and
a cam screw confiured to be inserted into one of the slidin ortion and the non-sliding portion, the cam screw having a tapered surface that is of varying camber configured to match fusion rods of different sizes;
wherein the tapered surface does not extend completely around a perimeter of the cam screw.

34. An adjustable spinal implant device according to claim 33, wherein the cam screw includes a cam retaining pin groove.

35. An adjustable spinal implant device according to claim 34, wherein the cam retaining pin groove has at least one locking point.

36. An adjustable spinal implant device according to claim 33, further comprising a prosthetic spinous process.

37. An adjustable spinal implant device according to claim 36, further comprising at least one soft tissue attachment hole located on the prosthetic spinous process.

38. An adjustable spinal implant device according to claim 36, wherein the sliding portion and the non-sliding portion extend transversely from the prosthetic spinous process.

39. An adjustable spinal implant device according to claim 36, wherein the sliding portion and the non-sliding portion are arched at least as much as the natural portions of the vertebra being replaced.

* * * * *

UNITED STATES PATENT AND TRADEMARK OFFICE
CERTIFICATE OF CORRECTION

PATENT NO. : 8,636,774 B2
APPLICATION NO. : 12/971620
DATED : January 28, 2014
INVENTOR(S) : Abrahams et al.

Page 1 of 1

It is certified that error appears in the above-identified patent and that said Letters Patent is hereby corrected as shown below:

In the Specification
In column 9 at lines 39-54, Delete "with respect....5A-5C.", and insert as continuation after --in paragraph--, on col. 9.

In the Claims
In column 17 at line 25, In Claim 11, change "implant" to --implant device--.
In column 17 at line 28, In Claim 12, change "implant" to --spinal implant device--.
In column 17 at line 30, In Claim 13, change "implant" to --implant device--.
In column 17 at line 48, In Claim 19, change "comprising;" to --comprising:--.
In column 17 at line 53, In Claim 19, change "slot and" to --slot; and--.
In column 17 at line 54, In Claim 19, change "confi ured" to --configured--.
In column 18 at line 16 (approx.), In Claim 27, change "comprising;" to --comprising:--.
In column 18 at line 22, In Claim 27, change "confi ured" to --configured--.
In column 18 at line 43, In Claim 33, change "comprising;" to --comprising:--.
In column 18 at line 46, In Claim 33, change "slidabl" to --slidably--.
In column 18 at line 47, In Claim 33, change "slot and" to --slot; and--.
In column 18 at line 48, In Claim 33, change "confi ured" to --configured--.
In column 18 at line 48, In Claim 33, change "slidin" to --sliding--.
In column 18 at line 49, In Claim 33, change "ortion" to --portion--.

Signed and Sealed this
Fifth Day of August, 2014

Michelle K. Lee
*Deputy Director of the United States Patent and Trademark Office*